(12) United States Patent
He et al.

(10) Patent No.: US 10,773,380 B2
(45) Date of Patent: Sep. 15, 2020

(54) ROBOTIC MANIPULATOR HAVING TWO DEGREES OF FREEDOM AND SURGICAL ROBOT

(71) Applicant: MICROPORT (SHANGHAI) MEDBOT CO., LTD., Shanghai (CN)

(72) Inventors: Chao He, Shanghai (CN); Tingping Dai, Shanghai (CN); Shuai Yuan, Shanghai (CN)

(73) Assignee: Microport (Shanghai) Medbot Co., Ltd., Shanghai (CN)

( * ) Notice: Subject to any disclaimer, the term of this patent is extended or adjusted under 35 U.S.C. 154(b) by 0 days.

(21) Appl. No.: 16/470,150

(22) PCT Filed: Dec. 15, 2017

(86) PCT No.: PCT/CN2017/116480
§ 371 (c)(1),
(2) Date: Jun. 14, 2019

(87) PCT Pub. No.: WO2018/108153
PCT Pub. Date: Jun. 21, 2018

(65) Prior Publication Data
US 2020/0016741 A1    Jan. 16, 2020

(30) Foreign Application Priority Data
Dec. 16, 2016  (CN) .......................... 2016 1 1169108

(51) Int. Cl.
*B25J 17/00* (2006.01)
*B25J 17/02* (2006.01)
(Continued)

(52) U.S. Cl.
CPC ............... *B25J 9/126* (2013.01); *A61B 34/30* (2016.02); *A61B 34/71* (2016.02); *B25J 9/106* (2013.01); *B25J 17/0258* (2013.01)

(58) Field of Classification Search
CPC ... B25J 18/00; B25J 9/126; B25J 9/106; B25J 17/0258
See application file for complete search history.

(56) References Cited

U.S. PATENT DOCUMENTS

2006/0074406 A1*  4/2006  Cooper ................. A61B 34/30
                                                                    606/1
2007/0089557 A1   4/2007  Solomon et al.
(Continued)

FOREIGN PATENT DOCUMENTS

CN   101862223 A   10/2010
CN   101889900 A   11/2010
(Continued)

OTHER PUBLICATIONS

International Search Report dated Mar. 14, 2018, in International Application No. PCT/CN2017/116480.

*Primary Examiner* — Jake Cook
(74) *Attorney, Agent, or Firm* — Muncy, Geissler, Olds & Lowe, P.C.

(57) ABSTRACT

A manipulator with two degrees of freedom and a surgical robot pivot a lower arm support under the driving of a second transmission structure so that a telescopic motion will be achieved with respect to a remote-center-of-motion (RCM); pivot a middle arm support under the driving of a first transmission structure and pivot an instrument assembly in the same way under the action of a first flexible member so that a pivoting motion will be achieved around the RCM. Therefore, the manipulator with two degrees of freedom is achieved.

14 Claims, 5 Drawing Sheets

(51) Int. Cl.
  *B25J 18/00* (2006.01)
  *B25J 9/12* (2006.01)
  *A61B 34/30* (2016.01)
  *A61B 34/00* (2016.01)
  *B25J 9/10* (2006.01)

(56) References Cited

U.S. PATENT DOCUMENTS

| | | | |
|---|---|---|---|
| 2007/0138992 | A1 | 6/2007 | Prisco et al. |
| 2007/0142969 | A1* | 6/2007 | Devengenzo .......... A61B 34/37 700/245 |
| 2008/0021440 | A1* | 1/2008 | Solomon ................ B25J 9/1045 606/1 |
| 2016/0346052 | A1 | 12/2016 | Rosielle et al. |

FOREIGN PATENT DOCUMENTS

| | | | |
|---|---|---|---|
| CN | 101919737 | A | 12/2010 |
| CN | 102764156 | A | 11/2012 |
| CN | 104224328 | A | 12/2014 |
| CN | 105250025 | A | 1/2016 |
| CN | 105287003 | A | 2/2016 |
| CN | 105358072 | A | 2/2016 |
| CN | 105748153 | A | 7/2016 |
| CN | 106037934 | A | 10/2016 |
| CN | 106584445 | A | 4/2017 |
| CN | 106618736 | A | 5/2017 |
| EP | 2612616 | A1 | 7/2013 |

* cited by examiner

ROBOTIC MANIPULATOR HAVING TWO DEGREES OF FREEDOM AND SURGICAL ROBOT

TECHNICAL FIELD

The present invention relates to minimally invasive surgical robots and/or manipulator of surgical robots and, in particular, to a manipulator with two degrees of freedom and a surgical robot.

BACKGROUND

Minimally invasive surgery is a new technique of surgical treatment using a slender laparoscopic or thoracoscopic and surgical instruments delivered into a patient's body through a small incision. It provides a range of advantages such as minimal invasion, slight pain, rapid recovery, short hospital stay and less hemorrhage. Despites so many advantages of minimally invasive surgery over the traditional open surgery, in the early days of this technique, operating space for the surgeon is limited for the smaller surgical incisions of body surface. Moreover, when a surgeon operates the surgical instruments under an endoscope, the manipulation directions of the surgical instruments is opposite to the desired ones as observed with the endoscope. Thus, difficulty of a surgery is increased and a surgeon can perform a minimally invasive surgical procedure dexterously after undergoing a long-term training.

With the development of robot-assisted minimally invasive surgery, minimally invasive surgical robots were provided as a good solution for the above issues. For example, with a teleoperation surgical robot, the surgeon can view two- or three-dimensional images of the patient's internal tissues captured by an endoscope and displayed on a display device of a master console. Also the images of the surgical site and two surgical instruments are displayed. And the surgeon can manipulate levers on the master console to teleoperation control manipulators and surgical instruments of the slave robot in a master-slave manner. With the assistance from the surgical robot, a minimally invasive surgical procedure can be accomplished with an enhanced operational accuracy, the same feelings and operations of the surgeon as in traditional open surgery which greatly reduce the operation complexity.

Currently, countries all over the world are actively doing research on surgical robotics, and a few products have been commercialized. A representative example of them is the da Vinci Surgical System developed by the Intuitive Surgical Inc., which is, however, bulky, complicated and expensive.

A prerequisite constraint for a surgical robot to perform a minimally invasive surgical procedure is to ensure that a surgical instrument mounted on the slave robotic manipulator is kept moving around a small incision on the patient's body during the operation, through which the surgical instrument comes into the patient's body. This requires the slave robotic manipulator to employ a remote-center-of-motion (RCM) mechanism.

Manipulator arrangements with such RCM mechanisms have been focus of research in the field of surgical robotics, but the existing solutions from the research have some deficiencies. For example, Chinese application No. CN103565529A describes a manipulator employing a double parallelogram mechanism, which provides that an end of an instrument mounted on the manipulator rotates around an RCM. This mechanism is, however, moveable with only one degree of freedom and the instrument is only allowed to pivot within a limited range. Chinese application No. CN101919739A describes another double parallelogram-base holder manipulator capable of moving in a larger space and providing an offset RCM. However, an instrument mounted on the manipulator is again only allowed to move around the RCM with one degree of freedom.

As noted above, both the above manipulators have an RCM at a distal end by a double parallelogram mechanism. However, each of these manipulators and the instrument mounted thereon is only able to move around the RCM with one degree of freedom, i.e., pivoting around the RCM. Adding a telescopic degree of freedom to the manipulators requires additional slidable components for enabling telescopic motion, that is to move toward or away from the RCM, which will expand the size of the manipulator and increase its design complexity.

Therefore, there is a need in the art for a manipulator with a telescopic movement with respect to an RCM and a pivotal movement around an RCM.

SUMMARY OF THE INVENTION

It is an object of the some of the embodiments to overcome the at least one of the above-described problems with the conventional manipulators, having only one degree of freedom, i.e., pivot around an associated remote-center-of-motion (RCM), by presenting a manipulator with two degrees of freedom and a surgical robot.

To this end, some embodiments provides a manipulator with two degrees of freedom, comprising a support structure, a first transmission structure, a second transmission structure and a linkage structure.

The support structure comprises a suspension support, an upper arm support, a middle arm support, a lower arm support and an instrument assembly.

The suspension support is rotatably coupled to the upper arm support via a first rotating shaft, and the upper arm support is rotatably coupled to the middle arm support via a second rotating shaft. The middle arm support is rotatably coupled to the lower arm support via a third rotating shaft, and the instrument assembly comprises a instrument holder and an instrument mounting cannula arranged on the instrument holder. The lower arm support is rotatably coupled to the instrument holder via a fourth rotating shaft, and the first rotating shaft has a rotational axis that is perpendicular to rotational axes of the second, third and fourth rotating shafts.

The first transmission structure is configured to control pivoting of the middle arm support relative to the upper arm support.

The second transmission structure is configured to control pivoting of the lower arm support relative to the middle arm support pivot.

The linkage structure comprises a slider, a first connecting rod, a second connecting rod, a third connecting rod and a third transmission structure.

The slider is rotatably coupled to the upper arm support via a fifth rotating shaft, and the first connecting rod is slidably coupled to the slider. The first connecting rod has a proximal side passing through the fifth rotating shaft. The second connecting rod is rotatably coupled at a proximal end thereof to the middle arm support via a sixth rotating shaft and is coupled to a proximal end of the third connecting rod via a seventh rotating shaft. The third connecting rod is rotatably coupled at a distal end thereof to the lower arm support via an eighth rotating shaft.

Connecting lines between rotational centers of the sixth, seventh, eighth and third rotating shafts define a parallelogram.

The third transmission structure comprises a first pulley, a second pulley, a third pulley, a fourth pulley and a first flexible member.

The second pulley is rotatably coupled to the second connecting rod via a ninth rotating shaft, and the second pulley is fixedly coupled to a distal end of the first connecting rod. The first pulley is rotatably coupled to the lower arm support via the fourth rotating shaft. The first pulley is able to rotate in synchronization with pivoting of the instrument holder. The second and first pulleys have equal diameters.

The third pulley is coupled to the seventh rotating shaft, and the fourth pulley is coupled to the eighth rotating shaft. The third and fourth pulleys have equal diameters. The first flexible member is respectively wound on the first and second pulleys. The first flexible member passes through the third and fourth pulleys on the sides thereof away from the instrument assembly.

A distance between rotational centers of the second and sixth rotating shafts is in a first ratio to a distance between the rotational centers of the second and third rotating shafts, which is configured at a first value. A distance between the rotational centers of the seventh and sixth rotating shafts is in a second ratio to a distance between rotational centers of the sixth and ninth rotating shafts, which is configured at the first value. A perpendicular line segment from the rotational center of the ninth rotating shaft to the proximal end side of the first connecting rod forms a first line segment, and a perpendicular line segment from the fourth rotating shaft to the instrument mounting cannula forms a second line segment. The first line segment has a length that is in a third ratio to a length of the second line segment. The third ratio is configured at the first value.

The seventh rotating shaft is positioned under a first connecting line formed by connecting the rotational centers of the sixth and ninth rotating shafts. The first connecting line forms a first angle with a second connecting line formed by connecting the rotational centers of the sixth and seventh rotating shafts. The first angle is configured at a first angular value. The sixth rotating shaft is positioned on a proximal side of a third connecting line formed by connecting the rotational centers of the second and third rotating shafts. The third connecting line forms a second angle with a fourth connecting line formed by connecting the rotational centers of the second and sixth rotating shafts. The second angle is configured at the first angular value. The second line segment forms a third angle with a parallel line that passes through the fourth rotating shaft and is parallel to the first line segment. The third angle is configured at the first angular value. The parallel line is able to be brought into coincidence with the second line segment if the line is pivoted clockwise by the first angular value.

Optionally, in the manipulator with two degrees of freedom, the first transmission structure may comprise a first power component, a tenth rotating shaft, a fifth pulley, a sixth pulley and a second flexible member, wherein:

the tenth rotating shaft is arranged on the upper arm support; the fifth pulley is arranged on the tenth rotating shaft; the sixth pulley is rotatably coupled to the upper arm support via the second rotating shaft and rotatable in synchronization with pivoting of the middle arm support; the second flexible member is respectively and fixedly coupled to the fifth and sixth pulleys; and the first power component has an output shaft that is coupled to the tenth rotating shaft so as to drive the tenth rotating shaft.

Optionally, in the manipulator with two degrees of freedom, the first transmission structure may further comprise a first brake component for braking the first transmission structure.

Optionally, in the manipulator with two degrees of freedom, the first brake component may be mounted at the tenth rotating shaft.

Optionally, in the manipulator with two degrees of freedom, the first rotating shaft may be arranged at a proximal end of the upper arm support.

Optionally, the manipulator with two degrees of freedom may further comprise a second power component having an output shaft to which the first rotating shaft is fixedly coupled, and/or a first bearing fitted over the first rotating shaft.

Optionally, in the manipulator with two degrees of freedom, the second transmission structure may comprise a third power component, an eleventh rotating shaft, a seventh pulley, an eighth pulley and a third flexible member, wherein:

the eleventh rotating shaft is arranged on the middle arm support; the seventh pulley is arranged on the eleventh rotating shaft; the eighth pulley is rotatably coupled to the middle arm support via the third rotating shaft and rotatable in synchronization with pivoting of the lower arm support; the third flexible member is respectively and fixedly coupled to the seventh and eighth pulleys; and the third power component has an output shaft that is coupled to the eleventh rotating shaft so as to drive the eleventh rotating shaft.

Optionally, in the manipulator with two degrees of freedom, the second transmission structure may further comprise a second brake component for braking the second transmission structure.

Optionally, in the manipulator with two degrees of freedom, the linkage structure may further comprise a fourth connecting rod which is rotatably coupled to the second connecting rod via a twelfth rotating shaft and rotatably coupled to the lower arm support via a thirteenth rotating shaft, wherein connecting lines between rotational centers of the seventh, eighth, thirteenth and twelfth rotating shafts define a parallelogram.

Optionally, the manipulator with two degrees of freedom may further comprise a base holder rotatably coupled to the suspension support via a fourteenth rotating shaft, wherein the fourteenth rotating shaft has a rotational axis that is perpendicular to the rotational axes of the second, third and fourth rotating shafts.

Optionally, in the manipulator with two degrees of freedom, the rotational axis of the fourteenth rotating shaft may be coplanar with the rotational axis of the first rotating shaft.

Optionally, in the manipulator with two degrees of freedom, the first value may be in a range of from $1/12$ to $1/2$.

Optionally, in the manipulator with two degrees of freedom, the first angular value may be in a range of from 0° to 30°.

The other embodiments provide a surgical robot comprising an instrument manipulator, wherein the instrument manipulator is implemented as any of the manipulators with two degrees of freedom as defined above.

In the manipulator and surgical robot of some embodiments, the lower arm support is pivoted under the driving of the second transmission structure so that a telescopic motion with respect to an RCM will be achieved. The middle arm support is pivoted under the driving of the first transmission structure and the instrument assembly is pivoted in the same way under the action of the first flexible member so that a pivoting motion around an RCM will be achieved. Therefore, the manipulator with two degrees of freedom is achieved.

In these figures: 10, a suspension support; 20, an upper arm support; 30, a middle arm support; 40, a lower arm support; 50, an instrument holder; 51, an instrument mounting cannula; 60, a base holder; 101, a first rotating shaft; 102, a second rotating shaft; 103, a third rotating shaft; 104, a fourth rotating shaft; 105, a fifth rotating shaft; 106, a sixth rotating shaft; 107, a seventh rotating shaft; 108, an eighth rotating shaft; 109, a ninth rotating shaft; 110, a tenth rotating shaft; 111, an eleventh rotating shaft; 112, a twelfth rotating shaft; 113, a thirteenth rotating shaft; 114, a fourteenth rotating shaft; 201, a first pulley; 202, a second pulley; 203, a third pulley; 204, a fourth pulley; 205, a fifth pulley; 206, a sixth pulley; 207, a seventh pulley; 208, an eighth pulley; 301, a first connecting rod; 302, a second connecting rod; 303, a third connecting rod; 304, a fourth connecting rod; 401, a first flexible member; 402, a second flexible member; 403, a third flexible member; 501, a slider; 601, a first power component; 602; a second power component; 603, a third power component; 701, a third brake; 702, a fourth brake; 801, a first bearing; 802, a second bearing; D, a remote-center-of-motion (RCM).

DETAILED DESCRIPTION

Specific embodiments of the manipulator with two degrees of freedom and surgical robot proposed in the present application will be described in detail with reference to the accompanying drawings. Advantages and features of the application will become more apparent from the following description, and from the appended claims. Note that the figures are much simplified and may not be drawn to scale, and the sole purpose of them is to facilitate easy and clear explanation of the embodiments. In particular, as these figures generally highlight different details, they tend to be drawn to different scales.

In the following embodiments, unless otherwise specified, a "distal end" refers to an end close to a remote-center-of-motion (RCM), while a "proximal end" refers to an end away from an RCM.

Embodiment 1

Figure 1:
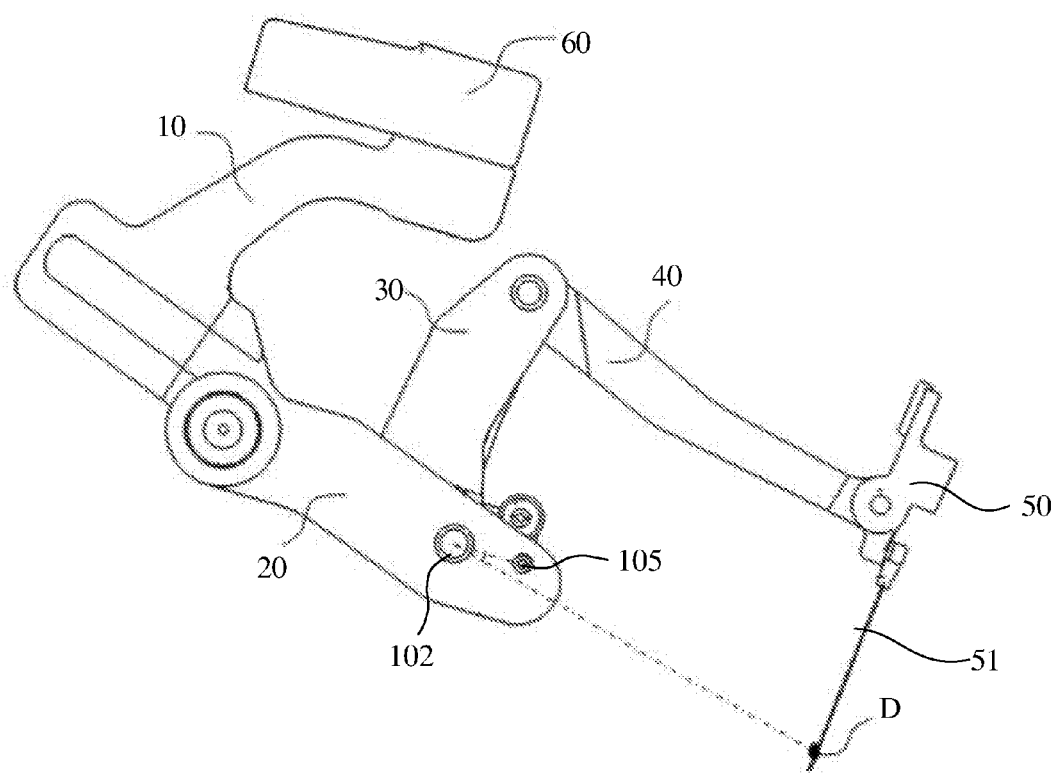
FIG. 1 is a structural schematic of a manipulator with two degrees of freedom according to a first embodiment.
Figure 2:
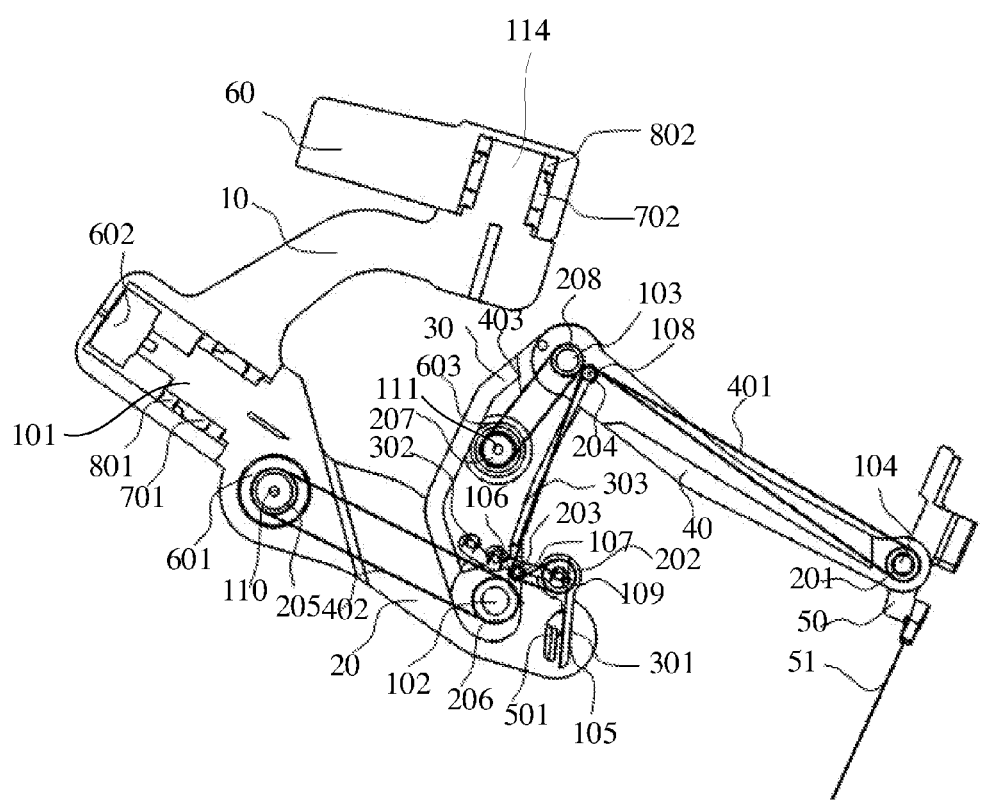
FIG. 2 is a diagram schematically illustrating the internal structure of the manipulator according to the first embodiment.
Figure 3:
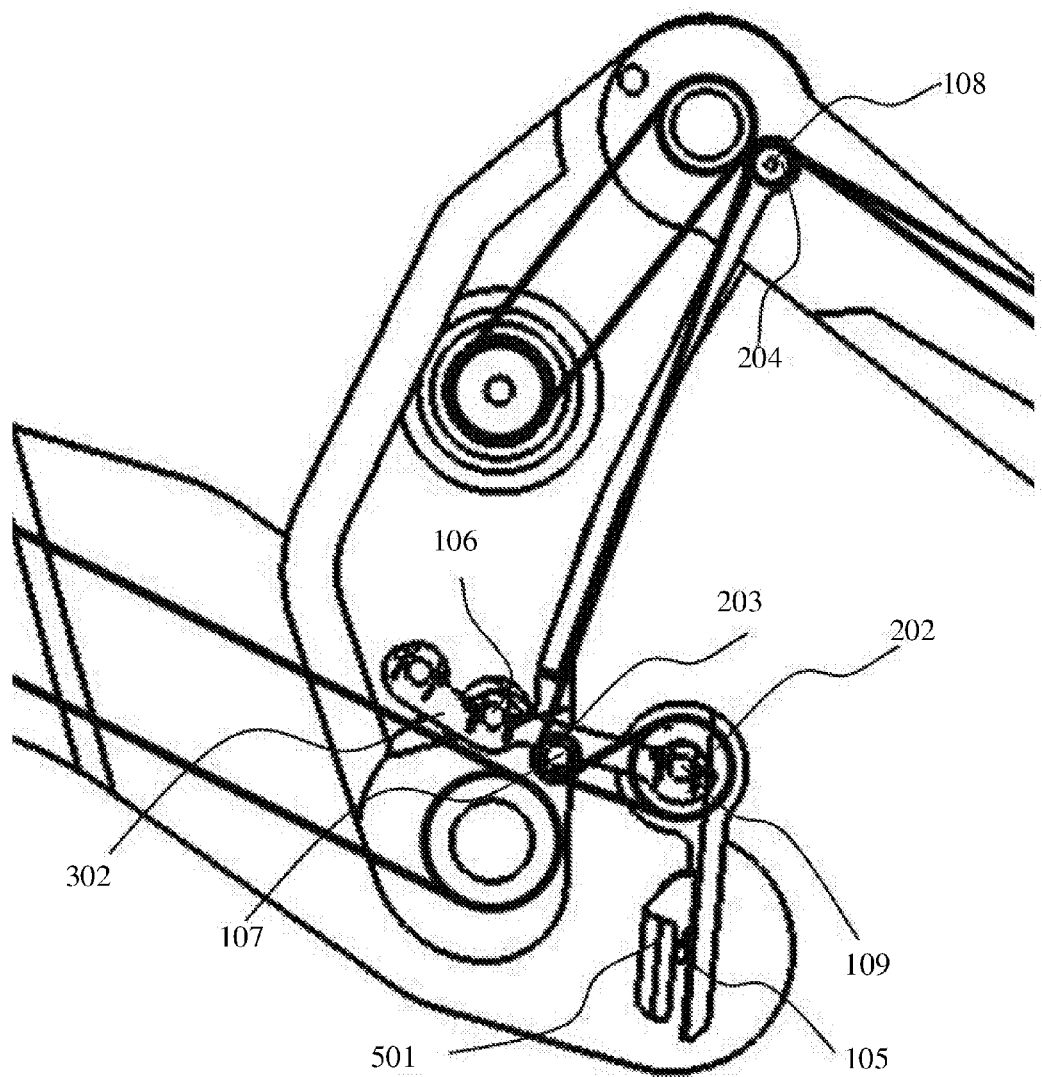
FIG. 3 is an enlarged view of a portion of the manipulator according to the first embodiment.

Reference is now made to FIGS. 1 through 3, in which FIG. 1 is a structural schematic of a manipulator with two degrees of freedom according to Embodiment 1 of the present application, FIG. 2 is a schematic cross-sectional view of the manipulator, and FIG. 3 is an enlarged view of a portion of the manipulator.

As shown in FIGS. 1-3, the manipulator with two degrees of freedom includes: a support structure for supporting the manipulator; a first transmission structure for driving the manipulator to pivot around a remote-center-of-motion (RCM); a second transmission structure for driving the manipulator to produce a telescopic motion with respect to the RCM; and a linkage structure for enabling a linkage of the articulated motions. With the assembly of these components, the manipulator is able to pivot around the RCM and telescope with respect to the RCM.

Specifically, the support structure includes a suspension support 10, an upper arm support 20, a middle arm support 30, a lower arm support 40 and an instrument assembly. The suspension support 10 is rotatably coupled to the upper arm support 20 via a first rotating shaft 101. The upper arm support 20 is rotatably coupled to the middle arm support 30 via a second rotating shaft 102. The middle arm support 30 is rotatably coupled to the lower arm support 40 via a third rotating shaft 103. The instrument assembly includes an instrument holder 50 and an instrument mounting cannula 51 arranged on the instrument holder 50. The lower arm support 40 is rotatably coupled to the instrument holder 50 via a fourth rotating shaft 104. The first rotating shaft 101 has a rotational axis that is perpendicular to rotational axes of the second, third and fourth rotating shafts 102, 103 and 104.

The suspension support 10 may be provided at its proximal end with a second power component 602 for driving the upper arm support 20 to pivot. In this embodiment, the "proximal end" of the suspension support 10 refers to the end of the suspension support 10 close to the upper arm support 20. The suspension support 10 may be further provided at its proximal end with a third brake 701 for braking the pivoting of the upper arm support 20. Specifically, the third brake 701 may be connected to both the suspension support 10 and the upper arm support 20. When the third brake 701 is deactivated, relative movement between the upper arm support 20 and the suspension support 10 is allowed. When the third brake 701 is activated, sufficient friction between the third brake 701 and the upper arm support 20 is created so that immobilization between the upper arm support 20 and the suspension support 10 is ensured. The suspension support 10 may further include a first bearing 801 configured to facilitate the support provided to the upper arm support 20 and reduce pivotal friction.

As noted above, the lower arm support 40 is coupled to the middle arm support 30 via the third rotating shaft 103. Additionally, the lower arm support 40 may be fixedly coupled to an eighth pulley 208 either via the third rotating shaft 103 or directly so that the lower arm support 40 can pivot in synchronization with the rotation of the eighth pulley 208. The fourth rotating shaft 104 is provided at a distal end of the lower arm support 40 and rotatably coupled to the instrument assembly.

As noted above, the instrument assembly includes the instrument holder 50 and the instrument mounting cannula 51 arranged thereon. The instrument holder 50 is rotatably coupled to the lower arm support 40 via the fourth rotating shaft 104. A perpendicular line segment from a rotational center of the fourth rotating shaft 104 to an axis of the instrument mounting cannula 51 is referred to as a "second line segment" hereinafter. It will be readily appreciated that the position of the axis of the instrument mounting cannula 51 can be known if the position and length of the second line segment are known.

The first transmission structure is configured to control pivoting of the middle arm support 30. The first transmission structure may include a first power component 601, a tenth rotating shaft 110, a fifth pulley 205, a sixth pulley 206 and a second flexible member 402. The tenth rotating shaft 110 may be arranged on the upper arm support 10, for example, at a proximal end of the upper arm support. The fifth pulley 205 is provided on the tenth rotating shaft 110. The sixth pulley 206 may be rotatably coupled to the upper arm support 20 via the second rotating shaft 102, and the middle arm support 30 may be rotatably coupled to the upper arm support 20 in synchronization with pivoting of the sixth pulley 206. For example, both the sixth pulley 206 and the middle arm support 30 may be fixedly coupled to the second rotating shaft 102, or alternatively the sixth pulley 206 may be directly coupled to the middle arm support 30, so as to allow their synchronous pivoting. The second flexible member 402 may be fixedly coupled to both the fifth and sixth pulleys 205, 206. In this embodiment, the term "fixed coupling" means that the second flexible member 402 is wound on the fifth and sixth pulleys 205, 206 in such a manner that there is no relative sliding between them, resulting in a constant transmission ratio between the fifth and sixth pulleys 205, 206. The first power component 601 may be configured to drive the tenth rotating shaft 110 and hence indirectly the middle arm support 30 via the fifth pulley 205, the second flexible member 402, the sixth pulley 206 and the second rotating shaft 102. Preferably, the first power component 601 may have an output shaft coupled to the tenth rotating shaft 110 either directly or via a transmission mechanism. The first transmission structure may further include a first brake component. When the first brake component is activated, the first transmission structure is in a brake state. In this embodiment, it is not limited to any particular location where the first brake component is mounted, as long as it is ensured that the first transmission structure is braked upon the activation of the first brake component. Also, in this embodiment, it is not limited to any particular component braked by the first brake component as long as one or more of the fifth pulley 205, the sixth pulley 206 and the second flexible member 402 may be braked thereby. In more details, the first brake component may be mounted coaxially with the tenth rotating shaft 110 so as to brake the tenth rotating shaft 110.

The second transmission structure is configured to control pivoting of the lower arm support 40. The second transmission structure may include a third power component 603, an eleventh rotating shaft 111, a seventh pulley 207, the eighth pulley 208 and a third flexible member 403. The eleventh rotating shaft 111 may be arranged on the middle arm support 30, for example, at a proximal end of the middle arm support, with the seventh pulley 207 being provided on the eleventh rotating shaft 111. In other words, the eleventh rotating shaft 111 may be arranged on the end of the middle arm support 30 close to the second rotating shaft 102. The eighth pulley 208 may be rotatably coupled to the middle arm support 30 via the third rotating shaft 103, and the lower arm support 40 may be rotatably coupled to the middle arm support 30 in synchronization with pivoting of the eighth pulley 208. For example, both the eighth pulley 208 and the lower arm support 40 may be fixedly coupled to the third rotating shaft 103, or alternatively the eighth pulley 208 may be directly coupled to the lower arm support 40, so as to allow their synchronous rotation and pivoting. The third flexible member 403 may be respectively fixedly coupled to the seventh and eighth pulleys 207, 208. In this embodiment, the term "fixed coupling" means that the third flexible member 403 is wound on both the seventh and eighth pulleys 207, 208 in such a manner that there is no relative sliding between them, resulting in a constant transmission ratio of the seventh and eighth pulleys 207, 208. The third power component 603 may have an output shaft coupled to the eleventh rotating shaft 111 so as to drive the eleventh rotating shaft 111 and hence indirectly the lower arm support 40 via the seventh pulley 207, the third flexible member 403, the eighth pulley 208 and the third rotating shaft 103. Preferably, the output shaft of the third power component 603 may be coupled to the eleventh rotating shaft 111 either directly or via a transmission mechanism. The second transmission structure may further include a second brake component configured to be activated to brake the second transmission structure. In this embodiment, it is not limited to any particular location where the second brake component is mounted, as long as it is ensured that the second transmission structure is braked upon the activation of the second brake component. Also, in this embodiment, it is not limited to any particular component braked by the second brake component as long as one or more of the seventh pulley 207, the eighth pulley 208 and the third flexible member 403 may be braked thereby. In more details the second brake component may be mounted coaxially with the eleventh rotating shaft 111 so as to brake the eleventh rotating shaft 111.

The linkage structure includes a slider 501, a first connecting rod 301, a second connecting rod 302, a third connecting rod 303 and a third transmission structure. The slider 501 is rotatably coupled to the upper arm support 20 via a fifth rotating shaft 105, and the first connecting rod 301 is slidably coupled to the slider 501 and passes through the fifth rotating shaft 105. More specifically, the first connecting rod 301 has a proximal side away from the instrument assembly and a distal side close to the instrument assembly, and a plane where the proximal side is located passes through the fifth rotating shaft 105. In this embodiment, the term "slidable coupling" means that the first connecting rod 301 and the slider 501 constitute a guide rail slider in which the first connecting rod 301 can only move in a direction constrained by the slider 501. The second connecting rod 302 is rotatably coupled at a proximal end thereof to the middle arm support 30 via a sixth rotating shaft 106 and is rotatably coupled to a proximal end of the third connecting rod 303 via a seventh rotating shaft 107. The third connecting rod 303 is rotatably coupled at a distal end thereof to the lower arm support 40 via an eighth rotating shaft 108. In this embodiment, the "proximal end" of the third connecting rod 303 refers to its end close to the second connecting rod 302, and the "distal end" of the third connecting rod 303 refers to its end away from the second connecting rod 302. Further, connecting lines between rotational centers of the sixth, seventh, eighth and third rotating shafts 106, 107, 108, 103 constitute a parallelogram.

The distance between rotational centers of the second and sixth rotating shafts 102, 106 is in a first ratio to the distance between rotational centers of the second and third rotating shafts 102, 103. The first ratio is configured at a first value. The distance between the rotational centers of the seventh and sixth rotating shafts 107, 106 is in a second ratio to the distance between rotational centers of the sixth and ninth rotating shafts 106, 109. The second ratio is also configured to at the first value. In addition, a perpendicular line segment from the rotational center of the ninth rotating shaft 109 to the proximal side of the first connecting rod 301 is referred to as a "first line segment". A perpendicular line segment from the rotational center of the fourth rotating shaft 104 to the instrument mounting cannula 51 is referred to as a "second line segment". A length of the first line segment is in a third ratio to a length of first line segment. The third ratio is also configured to at the first value which is preferably in the range of $\frac{1}{12}$-$\frac{1}{2}$, more preferably $\frac{1}{6}$.

The third transmission structure includes a first pulley 201, a second pulley 202, a third pulley 203, a fourth pulley 204 and a first flexible member 401. The second pulley 202 is rotatably coupled to the second connecting rod 302 via the ninth rotating shaft 109 and fixedly coupled to a distal end of the first connecting rod 301. The first pulley 201 is rotatably coupled to the lower arm support 40 via the fourth rotating shaft 104, and is fixedly coupled to the instrument holder 50 either via the fourth rotating shaft 104 or directly so that the instrument holder 50 can pivot in synchronization with rotation of the first pulley 201. The second and first pulleys 202, 201 have equal diameters. The third pulley 203 is coupled to the seventh rotating shaft 107, and the fourth pulley 204 is coupled to the eighth rotating shaft 108. The third and fourth pulleys 203, 204 have equal diameters. The first flexible member 401 is wound on the first and second pulleys 201, 202 tightly enough to make the first flexible member 401 move in synchronization with the first and second pulleys 201, 202 without relative displacement therebetween. The first flexible member 401 is also wound on the third and fourth pulleys 203, 204 on the sides thereof away from the instrument assembly.

In this way, a line connecting the tangent point where the first flexible member 401 leaves from the third pulley 203 and the tangent point where it comes into contact with the fourth pulley 204 is parallel to a connecting line between the rotational centers of the third and fourth pulleys 203, 204. That is, the first flexible member 401 is so wound on the third and fourth pulleys 203, 204 that it defines a first wrap angle at the third pulley 203 and a second wrap angle at the fourth pulley 204. In the event of a driving force acting on the slider 501, or when the first power component 601 is driving the fifth pulley 205, or when the third power component 603 is driving the seventh pulley 207, a change value of the first wrap angle will equal to a change value of the second wrap angle.

With continued reference to FIGS. 1 and 2, in this embodiment, the second connecting rod 302 is a folding rod. In more details, the seventh rotating shaft 107 is positioned under a first connecting line formed by the rotational centers of the sixth and ninth rotating shafts 106, 109. The first connecting line defines a first angle together with the second connecting line between the rotational centers of the sixth and seventh rotating shafts 106, 107, which is configured at a first angular value. That is, when the second connecting line is pivoted counterclockwise around the rotational center of the sixth rotating shaft 106 by the first angular value, it will comes into coincidence with the first connecting line. In this embodiment, the sixth rotating shaft 106 is positioned left to a third connecting line between the rotational centers of the second and third rotating shafts 102, 103. The third connecting line defines a second angle with a fourth connecting line formed by the rotational centers of the second and sixth rotating shafts 102, 106, which is also configured at the first angular value. That is, when the fourth connecting line is pivoted clockwise around the rotational center of the sixth rotating shaft 106 by the first angular value, it will comes into coincidence with the third connecting line. Additionally, a third angle defined between the second line segment and a parallel line that passes through the fourth rotating shaft 104 and extends in parallel to the first line segment is also configured at the first angular value. That is, this parallel line will be brought into coincidence with the second line segment when it is pivoted clockwise by the first angular value. Preferably, the first angular value is within the range of 0-30°, with 15° being more preferred. In this arrangement, when a connecting line between the rotational centers of the second and fifth rotating shafts 102, 105 is pivoted clockwise around the rotational center of the second rotating shaft 102 by the first angular value, it will intersect with the axis of the instrument mounting cannula 51, and the intersection point acts as a remote-center-of-motion (RCM) D (see FIG. 1).

In this embodiment, when the lower arm support 40 pivots under the driving of the third power component 603, a telescopic motion will be resulted with respect to the RCM D. Additionally, when the middle arm support 30 pivots under the driving of the first power component 601 and the instrument assembly pivots in the same way under the action of the first flexible member 401, a pivoting motion will be resulted around the RCM D. Therefore, the manipulator has both telescopic and pivotal degrees of freedom.

With continued reference to FIGS. 1 and 2, in this embodiment, the support structure of the manipulator with two degrees of freedom may further include a base holder 60 that is rotatably coupled to the suspension support 10 via a fourteenth rotating shaft 114 disposed at a distal end of the suspension support 10. The fourteenth rotating shaft 114 may have a rotational axis perpendicular to the axes of the second, third and fourth rotating shafts 102, 103 and 104. Preferably, the rotational axis of the fourteenth rotating shaft 114 may be coplanar with the rotational axis of the first rotating shaft 101. In this embodiment, the "distal end" of the suspension support 10 refers to the end thereof close to the base holder 60. Moreover, the base holder 60 may be provided with a second bearing 802 configured to facilitate the pivoting of the suspension support 10 and reduce pivotal friction. The base holder 60 may also be provided a fourth brake 702 for braking pivoting of the suspension support 10. Specifically, when the fourth brake 702 is deactivated, the fourth brake 702 may be configured to allow relative pivoting between the suspension support 10 and the base holder 60 and when the fourth brake 702 is activated, sufficient friction is created between the fourth brake 702 and the suspension support 10 so that immobilization between the suspension support 10 and the base holder 60 is ensured.

Figure 4:
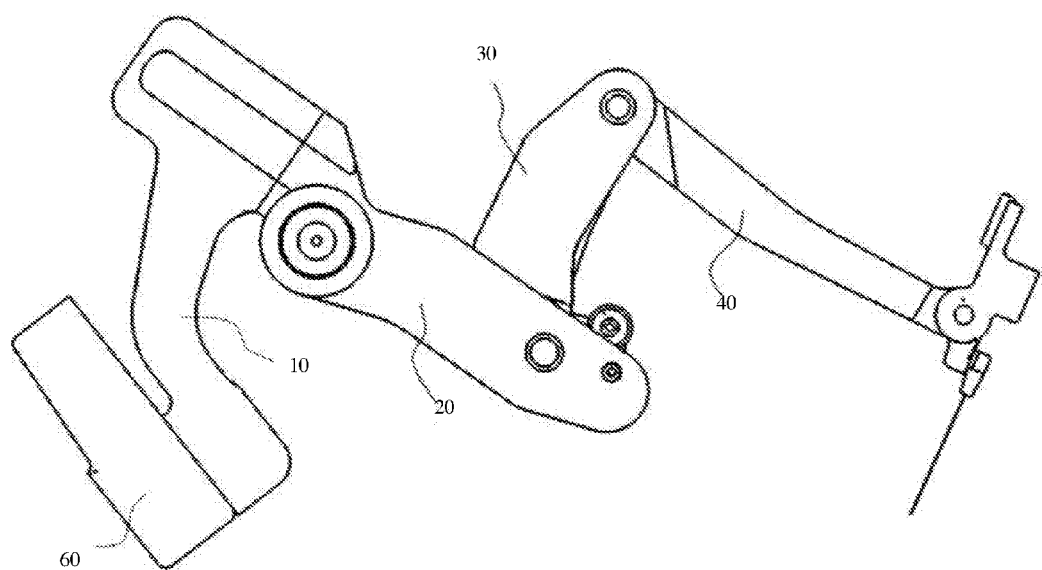
FIG. 4 is another structural schematic of the manipulator according to the first embodiment.

In this embodiment, the suspension support 10 is arranged below base holder 60, and also the upper arm support 20, the middle arm support 30, the lower arm support 40 and the instrument assembly are generally positioned under the base holder 60. In other embodiments, the suspension support 10 may also be arranged over the base holder 60 (see FIG. 4 for details). In this case, the upper arm support 20, the middle arm support 30, the lower arm support 40 and the instrument assembly are generally positioned above the base holder 60.

Embodiment 2

In this embodiment, the same or functionally identical elements are given the same reference numerals as Embodiment 1. The following description emphasizes the differences between these embodiments.

Figure 5:
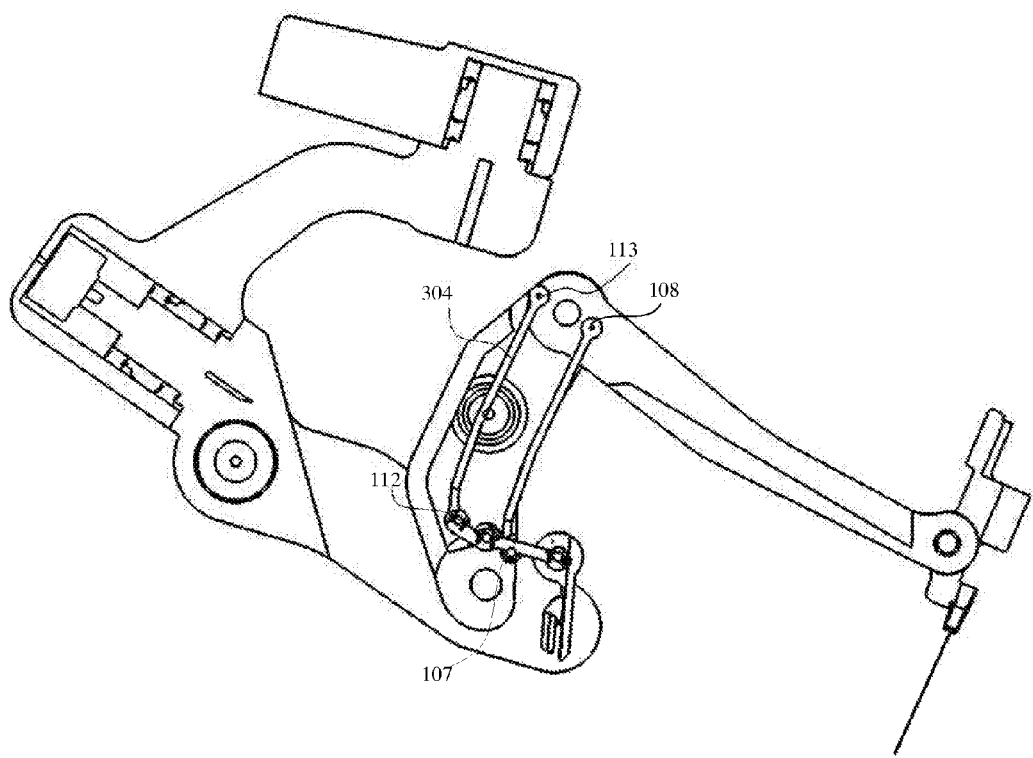
FIG. 5 is a structural schematic of a manipulator with two degrees of freedom according to a second embodiment.

With combined reference to FIGS. 5 and 2, Embodiment 2 differs from Embodiment 1 in that, in Embodiment 2, the linkage structure further includes a fourth connecting rod 304 which is rotatably coupled to the second connecting rod 302 via a twelfth rotating shaft 112 and rotatably coupled to the lower arm support 40 via a thirteenth rotating shaft 113. Connecting lines between rotational centers of the twelfth, thirteenth, seventh and eighth rotating shafts 112, 113, 107 and 108 constitute another parallelogram. The fourth connecting rod 304 enables a reinforcement structure with virtual constraints. Further, the fourth connecting rod 304 may be positioned on the side of the second connecting rod 302 away from the instrument assembly. Alternatively, the fourth connecting rod 304 may also be arranged on the side of the second connecting rod 302 close to the instrument assembly.

Also disclosed herein is a surgical robot comprising a surgeon-side end and a patient-side end. The patient-side end comprises a base holder, an adjustment manipulator, an instrument manipulator and a surgical instrument, where the instrument manipulator is implemented as any of the manipulators with two degrees of freedom as defined above.

The description presented above is merely that of some preferred embodiments of the present application and does not limit the scope thereof in any sense. Any and all changes and modifications made by those of ordinary skill in the art based on the above teachings fall within the scope as defined in the appended claims.

What is claimed is:

1. A manipulator with two degrees of freedom, comprising a support structure, a first transmission structure, a second transmission structure and a linkage structure, wherein:
the support structure comprises a suspension support, an upper arm support, a middle arm support, a lower arm support and an instrument assembly,
the suspension support rotatably coupled to the upper arm support via a first rotating shaft, the upper arm support rotatably coupled to the middle arm support via a second rotating shaft, the middle arm support rotatably coupled to the lower arm support via a third rotating shaft, the instrument assembly comprising an instrument holder and an instrument mounting cannula arranged on the instrument holder, the lower arm support rotatably coupled to the instrument holder via a fourth rotating shaft, the first rotating shaft having a rotational axis that is perpendicular to rotational axes of the second, third and fourth rotating shafts;
the first transmission structure is configured to control pivoting of the middle arm support relative to the upper atm support;
the second transmission structure is configured to control pivoting of the lower arm support relative to the middle arm support pivot;
the linkage structure comprises a slider, a first connecting rod, a second connecting rod, a third connecting rod and a third transmission structure, wherein:
the slider is rotatably coupled to the upper arm support via a fifth rotating shaft, the first connecting rod slidably coupled to the slider, the first connecting rod having a proximal end side passing through the fifth rotating shaft, the second connecting rod rotatably coupled at a proximal end thereof to the middle arm support via a sixth rotating shaft, the second connecting rod rotatably coupled to a proximal end of the third connecting rod via a seventh rotating shaft, the third connecting rod rotatably coupled at a distal end thereof to the lower arm support via an eighth rotating shaft;
connecting lines between rotational centers of the sixth, seventh, eighth and third rotating shafts constitute a parallelogram;
the third transmission structure comprises a first pulley, a second pulley, a third pulley, a fourth pulley and a first flexible member, wherein:
the second pulley is rotatably coupled to the second connecting rod via a ninth rotating shaft, the second pulley fixedly coupled to a distal end of the first connecting rod, the first pulley rotatably coupled to the lower arm support via the fourth rotating shaft, the first pulley rotating in synchronization with pivoting of the instrument holder, the second and first pulleys having equal diameters;
the third pulley is coupled to the seventh rotating shaft, the fourth pulley coupled to the eighth rotating shaft, the third and fourth pulleys having equal diameters, the first flexible member respectively wound on the first and second pulleys, the first flexible member passing through the third and fourth pulleys on sides thereof away from the instrument assembly;
a distance between rotational centers of the second and sixth rotating shafts is in a first ratio to a distance between the rotational centers of the second and third rotating shafts, the first ratio configured at a first value, a distance between the rotational centers of the seventh and sixth rotating shafts being in a second ratio to a distance between rotational centers of the sixth and ninth rotating shafts, the second ratio configured at the first value, a perpendicular line segment from the rotational center of the ninth rotating shaft to the proximal side of the first connecting rod forming a first line segment, a perpendicular line segment from the fourth rotating shaft to the instrument mounting cannula forming a second line segment, the first line segment having a length in a third ratio to a length of the second line segment, the third ratio configured at the first value; and
the seventh rotating shaft is positioned under a first connecting line formed by connecting the rotational centers of the sixth and ninth rotating shafts, the first connecting line forming a first angle with a second connecting line formed by connecting the rotational centers of the sixth and seventh rotating shafts, the first angle configured at a first angular value, the sixth rotating shaft positioned on a proximal side of a third connecting line formed by connecting the rotational centers of the second and third rotating shafts, the third connecting line forming a second angle with a fourth connecting line formed by connecting the rotational centers of the second and sixth rotating shafts, the second angle configured at the first angular value, the second line segment forming a third angle with a parallel line that passes through the fourth rotating shaft and is parallel to the first line segment, the third angle configured at the first angular value, wherein the parallel line is able to be brought into coincidence with the second line segment if the line is pivoted clockwise by the first angular value.

2. The manipulator with two degrees of freedom of claim 1, wherein the first transmission structure comprises a first power component, a tenth rotating shaft, a fifth pulley, a sixth pulley and a second flexible member,
the tenth rotating shaft arranged on the upper arm support, the fifth pulley arranged on the tenth rotating shaft, the sixth pulley rotatably coupled to the upper arm support via the second rotating shaft and rotatable in synchronization with pivoting of the middle arm support, the second flexible member respectively and fixedly coupled to the fifth and sixth pulleys, the first power component having an output shaft that is coupled to the tenth rotating shaft so as to drive the tenth rotating shaft.

3. The manipulator with two degrees of freedom of claim 2, wherein the first transmission structure further comprises a first brake component for braking the first transmission structure.

4. The manipulator with two degrees of freedom of claim 3, wherein the first brake component is mounted at the tenth rotating shaft.

5. The manipulator with two degrees of freedom of claim 1, wherein the first rotating shaft is arranged at a proximal end of the upper arm support.

6. The manipulator with two degrees of freedom of claim 5, further comprising:
  a second power component having an output shaft to which the first rotating shaft is fixedly coupled, and/or
  a first bearing fitted over the first rotating shaft.

7. The manipulator with two degrees of freedom of claim 1, wherein the second transmission structure comprises a third power component, an eleventh rotating shaft, a seventh pulley, an eighth pulley and a third flexible member,
  the eleventh rotating shaft arranged on the middle arm support, the seventh pulley arranged on the eleventh rotating shaft, the eighth pulley rotatably coupled to the middle arm support via the third rotating shaft and rotatable in synchronization with pivoting of the lower arm support, the third flexible member respectively and fixedly coupled to the seventh and eighth pulleys, the third power component having an output shaft that is coupled to the eleventh rotating shaft so as to drive the eleventh rotating shaft.

8. The manipulator with two degrees of freedom of claim 7, wherein the second transmission structure further comprises a second brake component for braking the second transmission structure.

9. The manipulator with two degrees of freedom of claim 1, wherein the linkage structure further comprises a fourth connecting rod which is rotatably coupled to the second connecting rod via a twelfth rotating shaft and rotatably coupled to the lower arm support via a thirteenth rotating shaft, and wherein connecting lines between rotational centers of the seventh, eighth, thirteenth and twelfth rotating shafts constitute a parallelogram.

10. The manipulator with two degrees of freedom of claim 1, further comprising a base holder rotatably coupled to the suspension support via a fourteenth rotating shaft, the fourteenth rotating shaft having a rotational axis that is perpendicular to the rotational axes of the second, third and fourth rotating shafts.

11. The manipulator with two degrees of freedom of claim 10, wherein the rotational axis of the fourteenth rotating shaft is coplanar with the rotational axis of the first rotating shaft.

12. The manipulator with two degrees of freedom of claim 1, wherein the first value is in a range of from $1/12$ to $1/2$.

13. The manipulator with two degrees of freedom of claim 1, wherein the first angular value is in a range of from 0° to 30°.

14. A surgical robot comprising an instrument manipulator, wherein the instrument manipulator is implemented as the manipulator with two degrees of freedom as defined in claim 1.

* * * * *